(12) United States Patent
Lee-Chen et al.

(10) Patent No.: US 9,629,835 B1
(45) Date of Patent: Apr. 25, 2017

(54) METHOD FOR TREATING TAU-ASSOCIATED DISEASES

(71) Applicant: NATIONAL TAIWAN NORMAL UNIVERSITY, Taipei (TW)

(72) Inventors: Guey-Jen Lee-Chen, Taipei (TW); Hsiu-Mei Hsieh, Taipei (TW); Guan-Chiun Lee, Taipei (TW); Ying-Chieh Sun, Taipei (TW)

(73) Assignee: National Taiwan Normal University, Taipei (TW)

( * ) Notice: Subject to any disclaimer, the term of this patent is extended or adjusted under 35 U.S.C. 154(b) by 0 days.

(21) Appl. No.: 15/238,025

(22) Filed: Aug. 16, 2016

(30) Foreign Application Priority Data

May 6, 2016 (TW) .............................. 105114059 A

(51) Int. Cl.
*A61K 31/535* (2006.01)
*A61K 31/47* (2006.01)
*A61K 31/4709* (2006.01)
*A61K 31/5377* (2006.01)

(52) U.S. Cl.
CPC ...... *A61K 31/4709* (2013.01); *A61K 31/5377* (2013.01)

(58) Field of Classification Search
CPC .............................. A61K 31/37; C07D 401/12
USPC ............................................. 514/235.2, 311
See application file for complete search history.

(56) References Cited

U.S. PATENT DOCUMENTS

| 8,198,300 | B2 | 6/2012 | Maccioni et al. |
| 2011/0269793 | A1* | 11/2011 | Maccioni ............... A61K 31/47 514/311 |
| 2013/0236395 | A1 | 9/2013 | Jones et al. |

OTHER PUBLICATIONS

Lu et al., "Syntheses, neural protective activities, and inhibition of glycogen synthase kinase-3b of substituted quinolines", Bioorganic & Medicinal Chemistry Letters, Jun. 4, 2014, vol. 24, pp. 3392-3397.

* cited by examiner

*Primary Examiner* — Raymond Henley, III
(74) *Attorney, Agent, or Firm* — Muncy, Geissler, Olds & Lowe, P.C.

(57) ABSTRACT

A method for treating tau-associated disease by administering a pharmaceutical composition comprising a quinoline derivative to a subject in need is disclosed. Particularly, a method for treating Alzheimer's disease by administering a pharmaceutical composition comprising a quinoline derivative to a subject in need is disclosed. The two disclosed quinoline derivatives have the inhibition effect for GSK-3β kinase activity, so as the two disclosed quinoline derivatives have the ability for inhibiting tau hyperphosphorylation or reducing tau aggregation.

7 Claims, 5 Drawing Sheets

METHOD FOR TREATING TAU-ASSOCIATED DISEASES

CROSS REFERENCE TO RELATED APPLICATION

This application claims the benefits of the Taiwan Patent Application Serial Number 105114059, filed on May 6, 2016, the subject matter of which is incorporated herein by reference.

BACKGROUND OF THE INVENTION

1. Field of the Invention

The present invention relates to a method for treating tau-associated diseases, particularly, to a method for treating Alzheimer's disease (AD).

2. Description of Related Art

Alzheimer's disease (AD) may cause progressive cognitive decline and memory loss, and the probability of suffering Alzheimer's disease increases with aging. With aging populations, the worldwide prevalence of AD will increase to more than 80 million by the year of 2040.

The reason and the mechanism of Alzheimer's disease remain unclear. Suggested mechanisms for the disorder include cholinergic hypothesis, amyloid hypothesis, and tau hypothesis. The most credible hypothesis is the abnormal tau aggregation. In this hypothesis, the imbalance between the catalytic activities of the kinase and phosphatase results in hyperphosphorylation of tau protein and forming the neurofibrillary tangles which disintegrate the microtubules in the neurons. Accordingly, the delivery system in the neurons will be destroyed, and resulting the death of the neurons.

Glycogen synthase kinase-3β (GSK-3β) is involved in the formation of hyperphosphorylated tau protein and is the main kinase that phosphorylates tau protein. Hence, GSK-3β can serve as a key target for treating Alzheimer's disease by inhibiting the activity of GSK-3β for alleviating tau aggregation.

Several GSK-3β inhibitors were disclosed by Phukan (2010) (Phukan et al., 2010. GSK-3β: Role in therapeutic landscape and development of modulators. Br. J. Pharmacol. 160, 1-19) which have been found and used in cell models and animal models for treating Alzheimer's disease. However, none of these GSK-3β inhibitors has passed the clinical trial for clinical therapy.

Therefore, it is desirable to provide a pharmaceutical composition which is effectively in inhibiting the activity of GSK-3β and preventing hyperphosphorylation of tau protein in neurons for treating Alzheimer's disease.

SUMMARY OF THE INVENTION

In order to solve the aforementioned problems, the present invention provides a method for treating tau-associated diseases, which are caused by the hyperphosphorylation of tau protein or tau aggregation, such as Alzheimer's disease.

To achieve the object, the present invention provides a method for treating tau-associated disease, which comprises: administering a pharmaceutical composition including a quinoline derivative to a subject in need, wherein the quinoline derivative has the following formula (I) or formula (II):

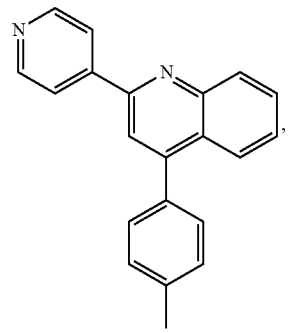

(I)

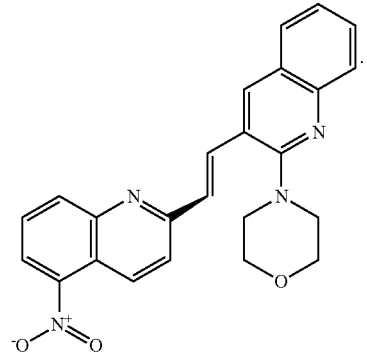

(II)

In the present invention, the concentration of the quinoline derivative represented by formula (I) or formula (II) in the pharmaceutical composition is not particularly limited and may be adjusted based on practical usage. For example, the concentration of the quinoline derivative in the pharmaceutical composition may be adjusted according to the severity of the disease or other conditions, so that the pharmaceutical composition administered to the subject in need may comprise a therapeutically effective amount of the quinoline derivative represented by formula (I); or may comprise a therapeutically effective amount of the quinoline derivative represented formula (II). In a preferred embodiment of the present invention, the concentration of quinoline derivative represented by formula (I) or formula (II) may be 1 nM to 100 µM; and in another preferred embodiment of the present invention, the concentration of the quinoline derivative represented by formula (I) or formula (II) may be 10 nM to 50 µM.

In the present invention, the tau-associated diseases may comprise those neurodegenerative diseases caused by hyperphosphorylation of tau protein or tau aggregation, especially for those neurodegenerative diseases that caused by hyperphosphorylation of tau protein or tau aggregation in neurons, glial cells, or Lewy bodies. For example, those diseases may be Alzheimer's disease, frontotemporal dementia (Pick's disease), progressive supranuclear palsy, Pugilistic dementia, Lytico-Bodig disease (Parkinson dementia complex), entangled oriented dementia, argyrophilic grain dementia, ganglioglioma, gangliocytoma, subacute sclerosing panencephalitis, lead brain lesions, tuberous sclerosis complex, Hallervorden-Spatz disease, and neuronal ceroid lipofuscinosis; wherein Alzheimer's disease and frontotemporal dementia are the most common tau-associated diseases.

Another subject of the present invention is to provide a method for treating Alzheimer's disease, which comprises the step of administering a pharmaceutical composition including a quinoline derivative, wherein the quinoline derivative has the following formula (I) or formula (II):

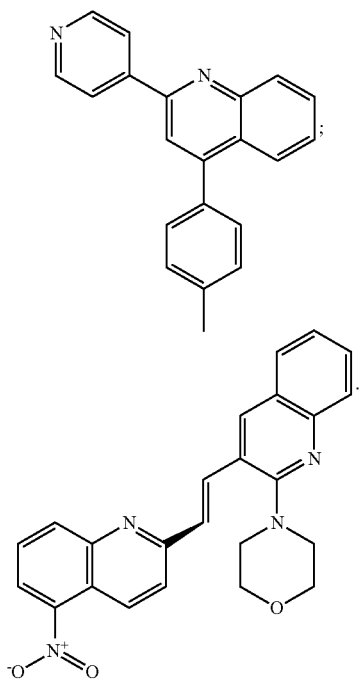

(I)

(II)

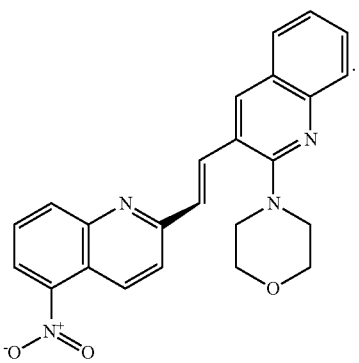

(I)

(II)

In the present invention, the concentration of the quinoline derivative represented by formula (I) or formula (II) in the pharmaceutical composition is not particularly limited and can be adjusted based on practical usage. For example, the concentration of the quinoline derivative represented by formula (I) or formula (II) in the pharmaceutical composition may be adjusted according to the severity of the disease or other conditions, so that the pharmaceutical composition administered to the subject in need may comprise a therapeutically effective amount of the quinoline derivative represented by formula (I) or formula (II). In a preferred embodiment of the present invention, the concentration of the quinoline derivative represented by formula (I) or formula (II) in the pharmaceutical composition may be 1 nM to 100 μM; and in another preferred embodiment of the present invention, the concentration of the quinoline derivative represented by formula (I) or formula (II) of the pharmaceutical composition may be 10 nM to 50 μM.

Also, the present invention provides a method for reducing hyperphosphorylation of tau protein or tau aggregation, which comprises the step of administering a pharmaceutical composition including a quinoline derivative, wherein the quinoline derivative has the following formula (I) or formula (II):

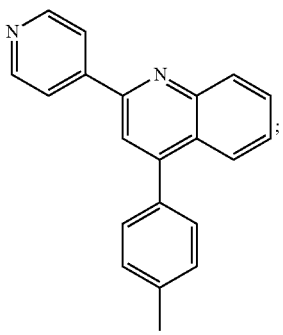

In the present invention, hyperphosphorylation of tau protein is reduced by the quinoline derivative through inhibiting glycogen synthase kinase-3β (GSK-3β) activity.

In the description of the present invention, the term "reduce", "decrease", "ameliorate", or "inhibit" used herein refers to the case that the pharmaceutical composition including the quinoline derivative represented by formula (I) or formula (II) of the present invention is applied to a subject suffering from the disease caused by hyperphosphorylation of tau protein or tau aggregation, or having a tendency of developing those aforementioned diseases, in order to achieve the treatment, mitigation, slowing, or improvement of the tendency of the diseases and symptoms.

In order to implement the method according to the present invention, the above pharmaceutical composition including the quinoline derivative represented by formula (I) or formula (II) can be delivered via oral administration, parental administration (such as subcutaneous injection, subdural injection, intravenous injection, intramuscular injection, intrathecal injection, intraperitoneal injection, intracranial injection, intra-arterial injection, or injection at morbid site), topical administration, rectal administration, nasal administration (such as aerosols, inhalants, or powders), sublingual administration, vaginal administration, or implanted reservoir, and so on; but the present invention is not limited thereto.

Hence, the pharmaceutical composition containing the aforementioned quinoline derivative represented by formula (I) or formula (II) can be formulated into health foods or clinical drugs for preventing or treating tau-associate diseases through any medicine manufacturing procedure. Based on the requirement or usage, the pharmaceutical composition of the present invention may further comprise at least one of a pharmaceutically acceptable carrier, a diluent, or an excipient in the art.

For example, the pharmaceutical composition may be formulated into a solid form or a liquid form. When the pharmaceutical composition is formulated into a solid form, the solid excipient may be powders, pellets, tablets, capsules, and suppositories. The pharmaceutical composition formulated into the solid form may further comprise solid formulations, such as flavoring agents, preservatives, disintegrants, flow aids, and fillers; but the present invention is not limited thereto. In addition, the liquid excipient of the pharmaceutical composition formulated in the liquid form may comprise water, solution, suspension, and emulsifier; and suitable coloring agents, flavoring agents, dispersing agents, antibacterial agents, and stabilizers may also be used to prepare the liquid formulations; but the present invention is not limited thereto.

Herein, the term "therapeutically effective amount" refers to the amount of the quinoline derivative represented by formula (I) or formula (II) needed for sufficiently inducing the desired medical or pharmaceutical effects. The therapeutically effective amount may be determined by skilled person in the art (such as doctors or pharmacists) by considering various factors such as body type, age, gender, health status, the specific disease involved, the severity of the disease involved, the patient's response, the administration routes, therapy, the co-administered drugs, or other relevant conditions.

In the description of the present invention, the terms "treating" or "treatment" refer to obtaining the desired medical and physiological effects. The medical or physiological effects may refer to preventing or partially preventing a disease, preventing a disease or symptoms of the disease, curing or partially curing a disease, or a therapy for symptoms caused by a disease or adverse effects caused by the disease. The terms "treating" or "treatment" refer to treatment of the mammals, particularly to human diseases. The scope of the treatment comprises preventing a disease, namely prophylactic treatment of a patient who is susceptible to but not yet diagnosed with the disease; inhibiting a disease, that is, inhibiting or reducing the development of a disease or its clinical symptoms; or alleviating a disease, that is, alleviating a disease and/or its clinical symptoms.

DETAILED DESCRIPTION OF THE PREFERRED EMBODIMENT

Statistical Analysis

Figure 1:
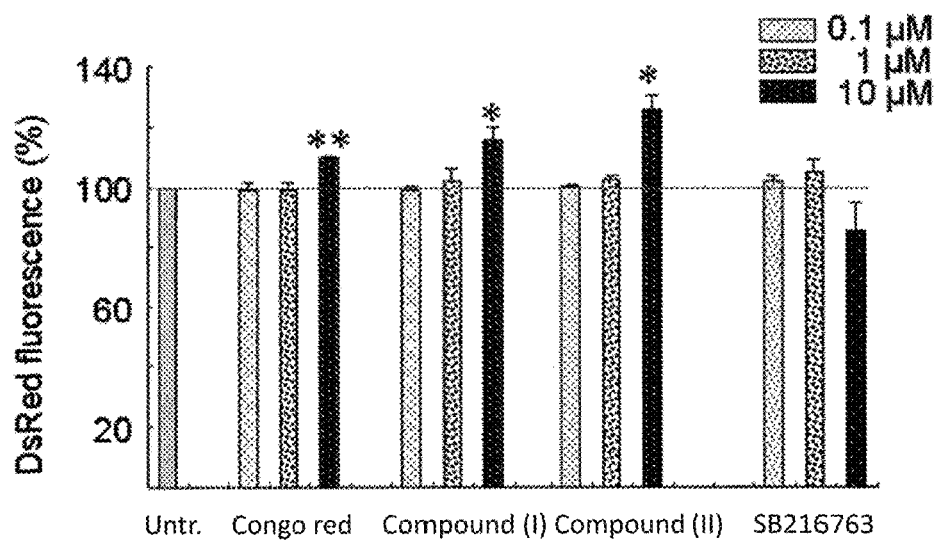
FIG. 1 is an analysis chart showing the DsRed fluorescence of cells of a preferred embodiment of the present invention.

For the following values, data are expressed as means±standard deviation (SD). More than three independent experiments were performed for each analysis, and differences between groups were evaluated using a Student's t-test. The p values were two-tailed and were considered statistically significant when p<0.05.

[Embodiment 1]—Evaluation of Inhibition of GSK-3β Activity

The inhibition ability of the quinoline derivatives represented by formula (I) (hereinafter compound (I)) and formula (II) (hereinafter compound (II)) were evaluated in the following paragraphs, wherein a known GSK-3β inhibitor SB216763 (Product No. S3442, Sigma) (compound (III)) serves as a positive control.

GSK-3β kinase activity was measured in the presence of the tested compounds (I) and (II) using ADP-Glo™ Kinase Assay system (Promega). Recombinant human GSK-3β (Product code V1991, Promega) was used as the enzyme source, and the GSK-3β substrate was derived from human muscle glycogen synthase 1 peptide (YR-RAAVPPSPSLSRHSSPHQ(pS)EDEEE) which corresponded to a region of glycogen synthase that was phosphorylated by GSK-3β. Reactions were performed at 30° C. for 30 minutes in the 25 μL mixture that contained 25 μM ATP, 0.2 mg/mL GSK-3β substrate, 1 ng of GSK-3β, and serial dilutions of compound (I), compound (II), or compound (III). Kinase activity data were measured as relative light units (RLU) directly correlated with the amount of ADP produced.

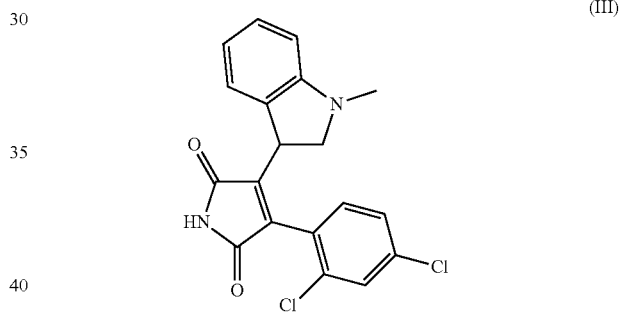

(III)

The IC$_{50}$ values of compound (I), compound (II), and compound (III) were determined by using SigmaPLOT software. Compound (III) is a known GSK-3β inhibitor in the art; the test results show that the IC$_{50}$ of compound (III) was 0.018 μM. When the concentration of compound (I) and compound (II) were 0.018 μM, the residual activities of GSK-3β of compounds (I) and (II) were 36.1±1.1%, and 90.9±6.6%, respectively. The IC$_{50}$ value of compound (I) was 0.0002 μM, and the residual activities of GSK-3β in the presence of the compound (II) with concentrations under its saturation solubility (<25 μM) were higher than 90%.

[Embodiment 2]—Evaluation of Inhibiting Hyperphosphorylation of Tau Protein

We used HEK-293 human cells expressing a DsRed-tagged proaggregation mutant (ΔK280) of the C-terminal repeat domain of tau (tau$_{RD}$-Gln$^{244}$-Glu$^{372}$ of the longest tau$^{441}$ isoform). The recombinant tau$_{RD}$-DsRed construct was under the control of a hybrid human cytomegalovirus (CMV)/TetO$_2$ promoter that can be induced by adding doxycycline. The Tet-On ΔK280tau$_{RD}$-DsRed293 cells were grown in medium containing blasticidin (5 μg/mL) and hygromycin (100 μg/mL) and were used for the following evaluation.

Tau$_{RD}$-DsRed 293 cells were plated into 96-well plates, grown for 24 h, and treated with 0.1, 1, 10 μM of congo red (a known tau aggregation inhibitor), compound (I), compound (II), and compound (III) (SB216763) for 8 h. Then doxycycline (Dox; 1 μg/mL) was added for 3 days and DsRed fluorescence was assessed using a high content analysis system (HCA) system (ImageXpressMICRO, Molecular Devices).

According to the fluorescence microscopy images of untreated cells, and cells treated with congo red, compound (I), compound (II), and SB216763, the quantification results are shown in FIG. 1 which were analyzed related to 100% fluorescence intensity of the untreated cells. As shown in FIG. 1, the fluorescence intensity of the cells treated with congo red (10 μM) was 110%; the fluorescence intensity of the cells treated with compound (I) (10 μM) was 116%, and the cells treated with compound (II) (10 μM) was 126%, whereas compound SB216763 has no effect on tau$_{RD}$-DsRed fluorescence. Based on the results that described above, compound (I) and compound (II) have the ability to decrease tau-aggregation in tau$_{RD}$-DsRed 293 cells (*p<0.05, **p<0.01).

Figure 2:
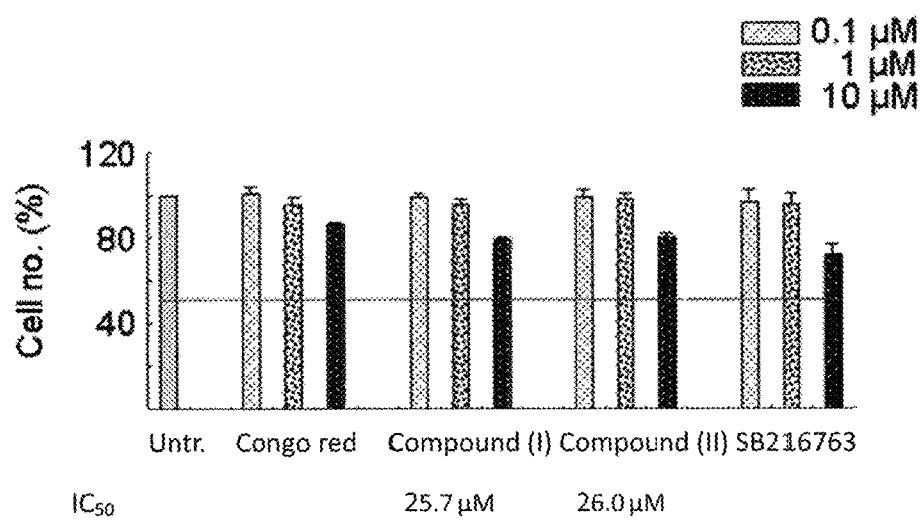
FIG. 2 is an analysis chart showing cell number and the cytotoxicity of the cells of a preferred embodiment of the present invention.

Also, IC$_{50}$ cytotoxicity of tau$_{RD}$-DsRed 293 cells is shown in FIG. 2, wherein the standard line represents 50% of viability. IC$_{50}$ of the compound (I) was 25.7 μM, and IC$_{50}$ of compound (II) was 26.0 μM.

[Embodiment 3]—Evaluation of Inhibiting Hyperphosphorylation of Tau Protein

We used human neuroblastoma cells (SH-SY5Y) expressing a DsRed-tagged proaggregation mutant (ΔK280) of the C-terminal repeat domain of tau (tau$_{RD}$-Gln$^{244}$-Glu$^{372}$ of the longest tau$^{441}$ isoform). The recombinant tau$_{RD}$-DsRed construct was under the control of a hybrid human cytomegalovirus (CMV)/TetO$_2$ promoter that can be induced by adding doxycycline. The Tet-On ΔK280 tau$_{RD}$-DsRed SH-SY5Y cells were grown in medium containing blasticidin (5 μg/mL) and hygromycin (100 μg/mL) and were then used for the following evaluation.

The expression levels of phosphorylated GSK-3β (p-GSK-3β, the non-active GSK-3β) and phosphorylated tau protein (p-tau) in cells were examined in the present embodiment for evaluating the ability of compound (I) and compound (II) for inhibiting hyperphosphorylation of tau protein. In order to examine the expression levels of p-GSK-3β and p-tau, western blotting analysis was applied with the following process.

First, SH-SY5Y tau$_{RD}$-DsRed cells were seeded in 6-well plates (1×10$^5$/well) in a medium containing all-trans retinoic acid (10 Sigma) for inducing the neural differentiation. After 24 hours of incubation, cells were pre-treated with 10 μM compound (I) or 10 μM compound (II) for 8 hours; after which, tau$_{RD}$-DsRed expression was induced with 1 μg/mL doxycycline for 7 days. Total proteins were extracted using RIPA buffer, which comprised 50 mM Tris-HCl, 150 mM NaCl, 1 mM EDTA, 1 mM EGTA, 0.1% SDS, 0.5% sodium deoxycholate, 1% Triton X-100, and a protease inhibitor cocktail from Calbiochem. 25 μM of total proteins were separated on 10% SDS-PAGE gels and blotted onto nitrocellulose membrane. After the non-specific antigens on the membrane were blocked by BSA, the antibodies against total GSK-3β (1:1000; Cell Signaling), p-GSK-3β (Ser9) (1:1000; Cell Signaling), total tau (1:500; Dako), p-tau (Ser202) (1:500; AnaSpec), p-tau (Thr231 and Ser396) (1:1000; Invitrogen), and GAPDH (1:2000; MDBio) were added and stained overnight in 4° C. Next, immunoreactive bands were detected using horseradish peroxidase-conjugated goat anti-mouse, goat anti-rabbit, or donkey anti-goat IgG antibodies (1:5000; GeneTex) and chemiluminescent substrate (Millipore) for evaluating the expression levels thereof in cells.

Figure 3:
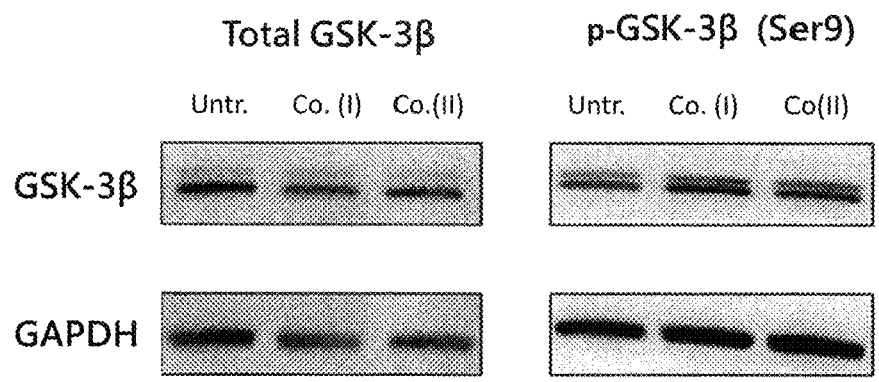
FIG. 3 is an analysis diagram showing the expressions of total GSK-3β and phosphorylated GSK-3β of a preferred embodiment of the present invention.
Figure 4:
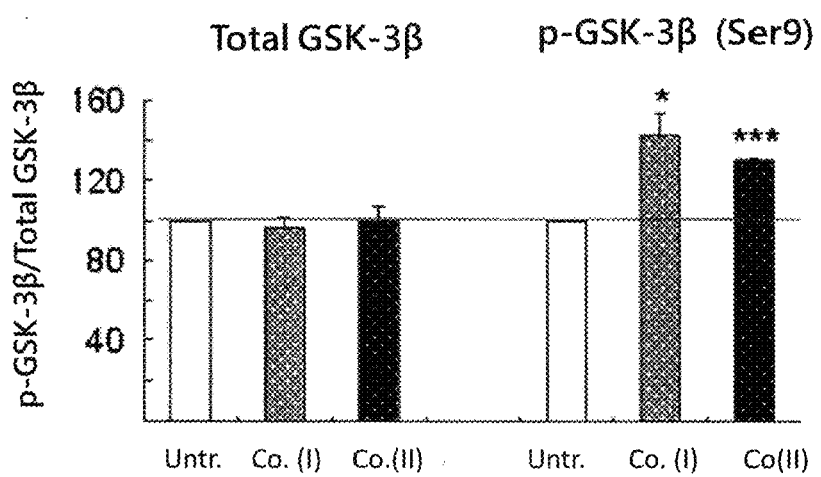
FIG. 4 is a quantification chart showing the expression levels of total GSK-3β and phosphorylated GSK-3β of a preferred embodiment of the present invention.

The expression levels of total GSK-3β and phosphorylated GSK-3β are shown in FIG. 3 and the quantifications thereof are shown in FIG. 4 (*p<0.05, *p<0.001). The results indicated that total GSK-3β expressions in untreated cells, the cells treated with compound (I), and the cells treated with compound (II) remained about the same without significant changes; however, the expression levels of phosphorylated GSK-3β (Ser 9**) in the cells treated with compound (I) and the cells treated with compound (II) were up-regulated relatively to that of the untreated cells. With respect to the untreated cells (100%), the expression level of phosphorylated GSK-3β at phosphorylation site Ser9 in cells was 143-130% (p=0.020-<0.001). Accordingly, it is proved that compound (I) and compound (II) may up-regulate the expression of phosphorylated GSK-3β in SH-SY5Y tau$_{RD}$-DsRed cells.

Figure 5:
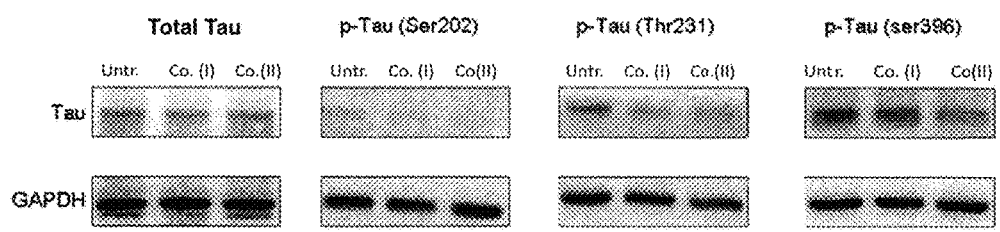
FIG. 5 is an analysis diagram showing the expressions of total tau and phosphorylated tau of a preferred embodiment of the present invention.
Figure 6:
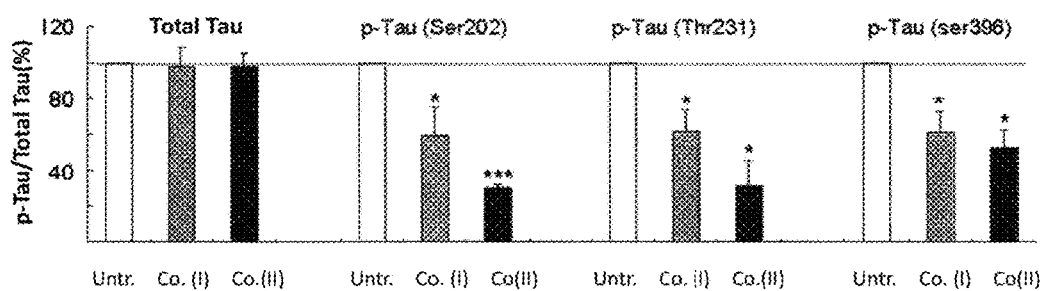
FIG. 6 is a quantification chart showing the expressions of total tau and phosphorylated tau protein of a preferred embodiment of the present invention.

In addition, the expression levels of total tau and phosphorylated tau protein (Ser202, Thr231, and Ser396) are shown in FIG. 5, and the quantifications thereof are shown in FIG. 6. According to the results, the expression levels of phosphorylated tau protein at three phosphorylated sites were down-regulated in cells treated with compound (I) and cells treated with compound (II). With respect to the expression level of the untreated cells (100%), the expression level of the phosphorylated tau protein at phosphorylated site Ser202 was 30%-59% (p=0.048-<0.001); the expression level of the phosphorylated tau protein at phosphorylated site Thr231 was 32%-62% (p=0.030-0.014); and the expression level of the phosphorylated tau protein at phosphorylated site Ser396 was 53%-61% (p=0.026-0.014).

Based on the aforementioned results, it is confirmed that compound (I) and compound (II) are effective in up-regulating the levels of phosphorylated GSK-3β for inhibiting GSK-3β activity, and thus decreasing the phosphorylation of tau protein in tau$_{RD}$-DsRed SH-SY5Y cells.

[Embodiment 4]—Mouse Hippocampal Primary Culture Under Tau Toxicity

The mouse hippocampal primary culture cells were isolated from the hippocampi of C57BL/6J mouse embryos at days 16-18. On days in vitro (DIV) 4 and 7, 2 μM of cytosine arabinoside was added to the culture medium to reduce the glial cell populations. On DIV 9, the cells were treated with 10 nM of Wortmannin (WT) and GF 109203X (GFX) to induce tau hyperphosphorylation to mimic an AD condition.

1 μM of compound (I) or compound (II) were then added to the cells at DIV 9. Cells were harvested 12 hours later for immunocytochemical staining with NeuN (for neuron) and MAP2 (for neurite morphology) antibodies.

Figure 7:
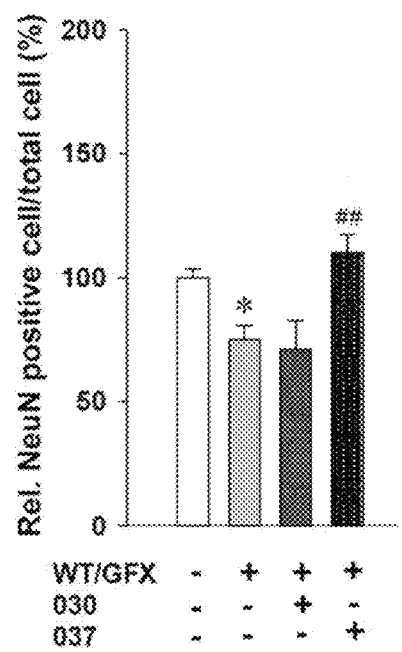
FIG. 7 is a quantification chart showing the relevant expression of NeuN of a preferred embodiment of the present invention.
Figure 8:
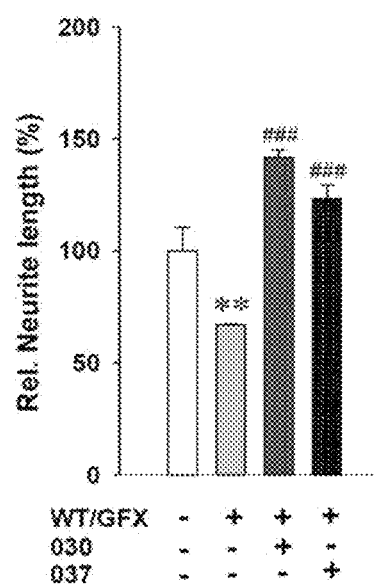
FIG. 8 is an analysis chart showing the relevant length of neurite of a preferred embodiment of the present invention.
Figure 9:
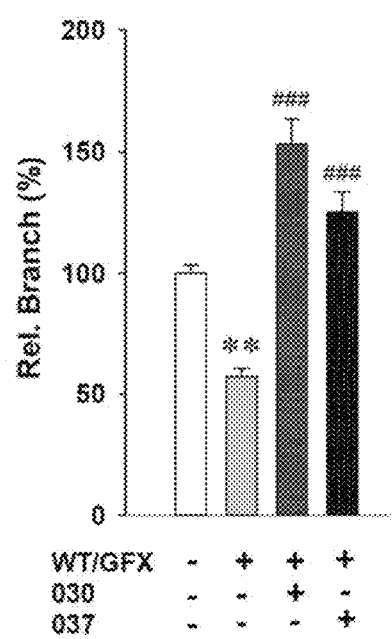
FIG. 9 is an analysis chart showing the relevant number of nerve branches of a preferred embodiment of the present invention.

The quantification of neuron numbers (NeuN relative expression levels), neurite outgrowth, and the relative number of neuron branches are shown in FIG. 7 to FIG. 9 (*, vs. control; #, vs. WT+GFX. * p<0.05; **/##p<0.01; ###p<0.001). The results showed that WT and GFX (WT/GFX) significantly down-regulated the neuronal survival and neurite length, and compound (I) and compound (II) have the ability to alleviate the reduction of neuronal survival rate, neurite length, and/or neurite branches induced by WT and GFX. The results indicated significant neuronal protective effects of compound (I) and compound (II).

According to the above evaluations, the quinoline derivatives represented by formula (I) and formula (II) of the present invention are effective in inhibiting GSK-3β activity. It is proved that quinoline derivatives represented by formula (I) and formula (II) are effective in reducing tau aggregation and hyperphosphorylation of tau protein in cell culture model. It is also confirmed that quinoline derivatives represented by formula (I) and formula (II) can protect hippocampal neurons against tau hyperphosphorylation induced by Wortmannin (WT) and GF-109203X (GFX) in mice. The demonstrated effect of the quinoline derivatives represented by formula (I) and formula (II) in reducing tau aggregation and the level of hyperphosphorylation of tau protein suggested that they have therapeutic potential in inhibiting or reducing the tau-associated diseases, such as Alzheimer's disease, frontotemporal dementia, or other neurodegenerative diseases, or its clinical symptoms, or has the effect of alleviating these diseases or its clinical symptoms.

What is claimed is:

1. A method for treating tau-associated disease, comprising: administering a pharmaceutical composition including a quinoline derivative to a subject in need, wherein the quinoline derivative has the following formula (I) or formula (II):

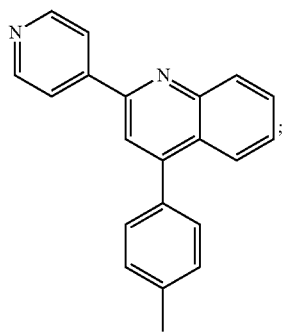
(I)

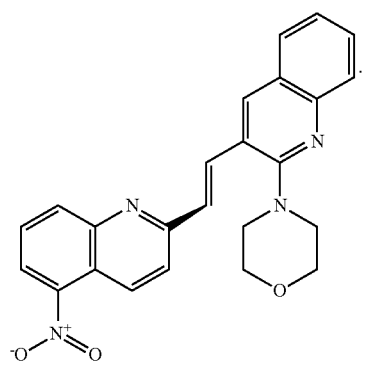
(II)

2. The method as claimed in claim 1, wherein the tau-associated disease is a neurodegenerative disease caused by hyperphosphorylation of tau protein or tau aggregation.

3. The method as claimed in claim 1, wherein the tau-associated disease is a neurodegenerative disease caused by hyperphosphorylation of tau protein or tau aggregation in neurons, glial cells, or Lewy bodies.

4. The method as claimed in claim 1, wherein the tau-associated disease is Alzheimer's disease or frontotemporal dementia.

5. A method for treating Alzheimer's disease, comprising: administering a pharmaceutical composition including a quinoline derivative to a subject in need, wherein the quinoline derivative has the following formula (I) or formula (II):

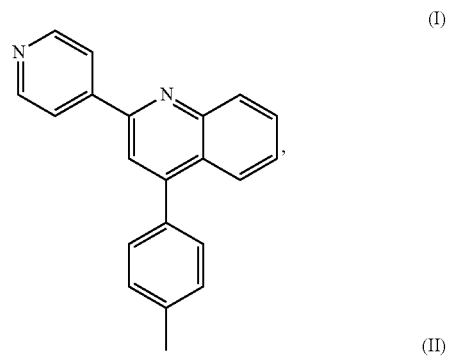
(I)

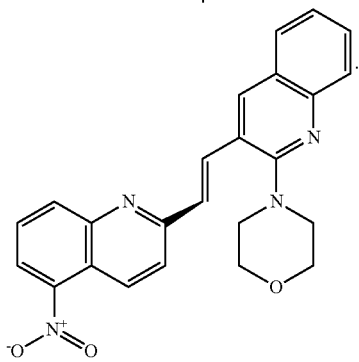
(II)

6. A method for reducing hyperphosphorylation of tau protein or tau aggregation, comprising: administering a pharmaceutical composition including a quinoline derivative to a subject in need, wherein the quinoline derivative has the following formula (I) or formula (II):

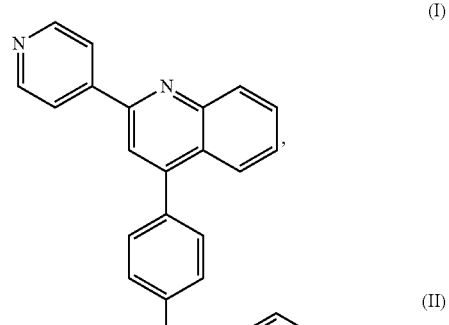
(I)

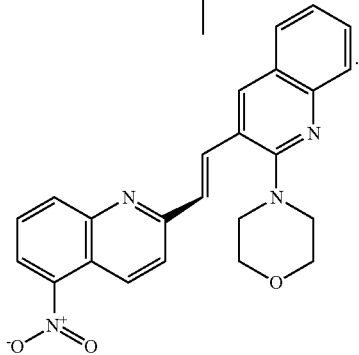
(II)

7. The method as claimed in claim 6, wherein hyperphosphorylation of tau protein is reduced by inhibiting glycogen synthase kinase-3β (GSK-3β) activity.

* * * * *